US008416416B2

(12) United States Patent
Zheng et al.

(10) Patent No.: US 8,416,416 B2
(45) Date of Patent: Apr. 9, 2013

(54) MEASURING METHOD FOR SPR AND SYSTEM THEREOF

(75) Inventors: Zheng Zheng, Beijing (CN); Yuhang Wan, Beijing (CN); Xin Zhao, Beijing (CN); Jinsong Zhu, Beijing (CN); Jiangfeng Fan, Beijing (CN)

(73) Assignees: National Center for Nanoscience and Technology, Beijing (CN); Beihang University, Beijing (CN)

( * ) Notice: Subject to any disclaimer, the term of this patent is extended or adjusted under 35 U.S.C. 154(b) by 0 days.

(21) Appl. No.: 12/745,444

(22) PCT Filed: Nov. 29, 2007

(86) PCT No.: PCT/CN2007/003369
§ 371 (c)(1),
(2), (4) Date: May 30, 2010

(87) PCT Pub. No.: WO2009/070913
PCT Pub. Date: Jun. 11, 2009

(65) Prior Publication Data
US 2010/0321697 A1 Dec. 23, 2010

(30) Foreign Application Priority Data
Nov. 29, 2007 (WO) ............... PCT/CN2007/003369

(51) Int. Cl.
*G01N 21/55* (2006.01)
(52) U.S. Cl.
USPC ........................................................ 356/445
(58) Field of Classification Search .......... 356/445–448, 356/451, 456, 301, 432, 337, 73.1; 385/12, 385/123
See application file for complete search history.

(56) References Cited

U.S. PATENT DOCUMENTS

| 5,375,011 | A | * | 12/1994 | Normandin et al. | 359/345 |
| 6,067,150 | A | * | 5/2000 | Beller et al. | 356/73.1 |
| 6,459,479 | B1 | * | 10/2002 | Lee et al. | 356/73.1 |
| 7,330,301 | B2 | * | 2/2008 | Harter | 359/333 |
| 7,385,683 | B2 | * | 6/2008 | Ozcan et al. | 356/73.1 |
| 2003/0086647 | A1 | * | 5/2003 | Willner et al. | 385/37 |
| 2005/0219543 | A1 | * | 10/2005 | Uehara et al. | 356/450 |
| 2006/0192969 | A1 | * | 8/2006 | Marks et al. | 356/451 |
| 2006/0205092 | A1 | * | 9/2006 | Lackritz et al. | 436/525 |
| 2007/0139648 | A1 | * | 6/2007 | Singh | 356/337 |
| 2007/0166763 | A1 | * | 7/2007 | Ho et al. | 435/7.1 |

* cited by examiner

*Primary Examiner* — Sang Nguyen
(74) *Attorney, Agent, or Firm* — Choate Hall & Stewart LLP; Brenda Herschbach Jarrell; William R. Haulbrook

(57) ABSTRACT

The invention provides an SPR measuring method and a measuring system thereof. According to the measuring method, first, a linear-polarized coherent broadband pulsed light beam is incident onto a surface of a sample under detection of a SPR sensing device to cause reflection; next, a time-domain monotonous chirp is performed on the incident coherent broadband pulsed light and/or the SPR reflected light; finally, the time-domain monotonically chirped SPR reflected light beam is detected, and information of the SPR effect is obtained according to the detected signal. According to the invention, the spectrum detection method used in conventional slow wavelength interrogation is converted into the high-speed real-time detection of time-domain pulse shape signals. Thus, the procedure of the SPR reaction may be monitored closely, and dynamical curves with very high time resolution may be obtained, in that case, fast biochemical reaction procedures may be monitored. As each part of the measuring system may remain fixed during the measurement, a compact, miniature and portable system may be realized. The interrogation part of the sensing system is easy-to-realize, of low cost and compatible with various SPR devices and components.

15 Claims, 4 Drawing Sheets

MEASURING METHOD FOR SPR AND SYSTEM THEREOF

FIELD OF THE INVENTION

The present invention relates to the field of sensor and sensing techniques, and more specifically to a measuring method for Surface Plasmon Resonance (SPR) and a measuring system for implementing the method.

BACKGROUND OF THE INVENTION

The Surface Plasmon (SP) is a propagating electron density wave occurring at the interface between metal and dielectric. Essential for the generation of SPs is the presence of free electrons at the interface of two materials, as a result of the analysis by Maxwell's equations, the materials' (usually a metal and a dielectric) dielectric constants have opposite signs. The field intensity is at its maximum at the interface, and decays exponentially in the normal direction on both sides of the surface. And the field is strongly bound to the interface. The dispersion relation of the SP waves is expressed as:

$$k_{sp} = \frac{2\pi}{\lambda}\left(\frac{\varepsilon_1\varepsilon_2}{\varepsilon_1+\varepsilon_2}\right)^{1/2} = \frac{\omega}{c}\left(\frac{\varepsilon_1\varepsilon_2}{\varepsilon_1+\varepsilon_2}\right)^{1/2} \quad (1)$$

where $k_{sp}$ is the wave vector of the SP waves on the metal surface, $\lambda$, $\omega$, c are the wavelength, angular frequency of the SP waves and the velocity of the light, respectively, and $\varepsilon_1$ and $\varepsilon_2$ are the dielectric constants of the metal layer and the dielectric layer, respectively.

Surface Plasmon Resonance (SPR) is a phenomenon in physical optics. The SPs can be excited by the evanescent waves generated through the total internal reflection occurs at the prism interface, and the energy can be coupled from the light waves to the surface plasmon waves. When a p-polarized planar light wave is incident on a dielectric/metal interface at a specific angle, where the evanescent wave vector matches with that of the surface plasmon, the energy of the incident light is coupled to the SP waves and the SPR is excited, in which case, the energy of the reflected light is significantly reduced. The phase matching relation of the SPR can be expressed as:

$$k_x = k\sin\theta = k_{sp} \quad (2)$$

It can be seen from Equations (1) and (2) that for the same dielectric under detection, the condition for the SPR excitation is a function of both the wavelength and the incident angle of the incident light. Thus, all the interrogation methods currently applied for the SPR detection are based on changing the incident light. These interrogation methods generally involve angular interrogation, wavelength interrogation, intensity interrogation and phase interrogation, among which the first two are mostly used.

1. Angular Interrogation: this is an interrogation method most commonly used in the conventional SPR sensor. In this method, a fixed-wavelength light source is used, and a mechanical device is used to rotate the SPR detection mechanism or the incident light source. So the SPR resonance angle can be found by changing the incident angle. Though the Angular Interrogation is straightforward and simple, and it can achieve the highest precision among all the currently available interrogation methods, the interrogating speed of the scanning system is limited by that of the precise mechanical rotating stage which is very low. Thus, it is difficult to realize fast real-time measurement with high time resolution.

2. Wavelength Interrogation: in this method, the incident angle is fixed, a quasi-planar beam of a broadband light source is used as the incident beam, and the spectrum of the reflected light is measured by using a spectrometer or a monochromator. In that case, the intensity of the response over a range of wavelengths can be obtained, and the corresponding SPR wavelength can be obtained. At an operational band of longer wavelength, the system precision of this method may reach or be even higher than that of the angular interrogation method. However, the speed of the currently available spectrometer is rather slow, which limits the interrogation speed of the system in the method. As a result, the interrogation frequency is very low and the realization of real-time detection for fast-changing signals is not possible.

It can be seen from the above-described SPR interrogation methods that the sensing detection system using the SPR effect has the following technical defects: low interrogation speed, bulky device, and not being able to realize high density multi-channel parallel detections and so on.

SUMMARY OF THE INVENTION

Therefore, it is an object of the invention to provide an SPR measuring method.

Another objective of the invention is to provide a measuring system using the above measuring method.

According to the present invention, an SPR measuring method comprises the steps of:

(1) providing a linear-polarized, coherent broadband pulsed light beam to incident upon a surface of a sample under detection of a SPR sensing device to cause reflection;

(2) applying a time-domain monotonous chirp to the incident coherent broadband pulsed light beam or the reflected coherent broadband pulsed light beam from the SPR sensing device; and (3) detecting the time-domain monotonous chirped SPR reflected light beam to obtain a first time-domain signal, detecting the coherent broadband pulsed light beam not affected by SPR effect of the sample but chirped with the time-domain monotonous chirp to obtain a second time-domain signal, obtaining wavelength information of the SPR according to the first time-domain signal and the second time-domain signal.

In accordance with the present invention, the first and second time-domain signals are compared to obtain a dip in time position corresponding to a change in the time-domain signals; then the time position in the pulseshape is mapped to the wavelength in the spectrum due to the monotonous chirping; thus the reflected spectrum modulated by the SPR effect is obtained, and the relative SPR wavelength information is obtained.

In accordance with the present invention, the incident coherent broadband pulsed light beam can be monotonous chirped in the time domain, so can the reflected coherent broadband pulsed light beam from the SPR sensing device.

Furthermore, the method comprises a step (4) of retrieving SPR information of the sample under detection, such as a change in refractive index, according to the data processing method used in wavelength interrogation.

In accordance with the present invention, the time-domain monotonous chirp is preferably linear.

In accordance with the present invention, the incident angle of the coherent broadband pulsed light is incident on the surface of the SPR sensing device at a fixed angle.

The present invention also provides an SPR measuring system, which comprises a coherent broadband pulsed light source that generates linear-polarized light, a dispersive device that generates a time-domain monotonous chirp, an SPR sensor device under detection, a first detector for receiving SPR reflected light and a data processing system for processing a detection result of the first detector, wherein the dispersive device is arranged in a light path before the first detector, which is, the dispersive device is arranged in a light path either between the coherent broadband pulsed light source and the SPR sensor device under detection, or between the SPR sensor device and the first detector.

The above measuring system may further include a second detector, and in that case the dispersive device is arranged in a light path between the coherent broadband pulsed light source and the SPR sensor device under detection. A beam-splitter for splitting the incident light into a plurality of beams is further arranged in the light path between the dispersive device and the SPR device. After the beam is split, at least one of the split beams is incident on the SPR device to be detected, and at least a further beam of the split beams is directly received by the second detector, and detection results of the first and second detectors are processed by the data processing system.

In the above measuring system, the coherent broadband pulsed light source may be a supercontinuum source or a mode-locked laser.

The dispersive device may choose the device that can generate a time-domain monotonous linear chirp.

The dispersive device may be selected from optical fiber, chirped fiber grating, grating pair, prism pair or ultrashort pulse shaper. The optical fiber may be normal single-mode fiber or dispersion compensation fiber and so on.

The detector may be high-speed photodetector, which comprises PIN detector and APD detector.

The beam-splitter may be optical beamsplitter or directional splitting fiber coupler.

The measuring method of SPR sensing and the measuring system thereof in the present invention have the following advantages:

1. According to the invention, the conventional wavelength interrogation is converted into the high-speed detection of time-domain pulse signals, and the high-speed SPR interrogation can be realized. The speed of interrogation can be improved by several orders of magnitude compared with the existing SPR detection methods. The present invention is based on the coherent broadband light source, in that case, for the short pulses repeated at a certain frequency, one measurement may be performed for each pulse, and the speed of interrogation can reach the repeat frequency of the broadened pulse. The repeat frequency generated by the existing coherent broadband light source is generally over tens of MHz, and sometimes above 10 GHz.

2. The invention can be used to monitor the procedure of the SPR reaction closely, and dynamical curves with very high time resolution may be obtained. The speed of interrogation is very high, thus, for the SPR reaction procedure, one measurement takes the duration of a chirped pulse, which may be extremely short (as short as in the order of ns or ps). Therefore, the whole SPR reaction procedure may be monitored over a fine time axis, thereby obtaining precise dynamical curves.

3. The invention can be used to monitor fast bio-chemical reaction procedures. SPR sensing devices are mostly applied for biochemical detections, among which a branch of special interest is to dynamically monitor the bio-chemical reaction procedures and then to obtain biodynamical information. Due to the limitation of the interrogation speed of the existing SPR sensing system, it is difficult to dynamically monitor the procedure of a biochemical reaction with short reaction time (in the order of a second or less). The invention may improve the interrogation speed significantly; besides, resolution in the time axis of the dynamical curves may be improved enormously. Even the fast biochemical reactions may be monitored dynamically using continuous high-speed interrogation.

4. In the sensing system accomplished according to the method of the invention, the light source, detection structure, photo-detector in the interrogation section ought to be fixed, which facilitates the realization of a compact, miniature and portable system.

5. In the interrogation section of the sensing system as accomplished according to the method of the invention, instead of an array of high-speed detectors, only one high-speed photo-detector is needed for each signal branch, which may be easily realized with low cost.

6. The method of the invention is compatible with various SPR sensing devices and components, such as conventional single-layer SPR structure, Long Range SPR (LRSPR), Coupled Plasmon Waveguide Resonance (CPWR), Waveguide Coupled SPR (WCSPR), and can be easily applied to these devices.

BRIEF DESCRIPTION OF THE DRAWINGS

In the following, embodiments of the invention will be described in detail in conjunction with the accompanying drawings, in which.

Figure 1:
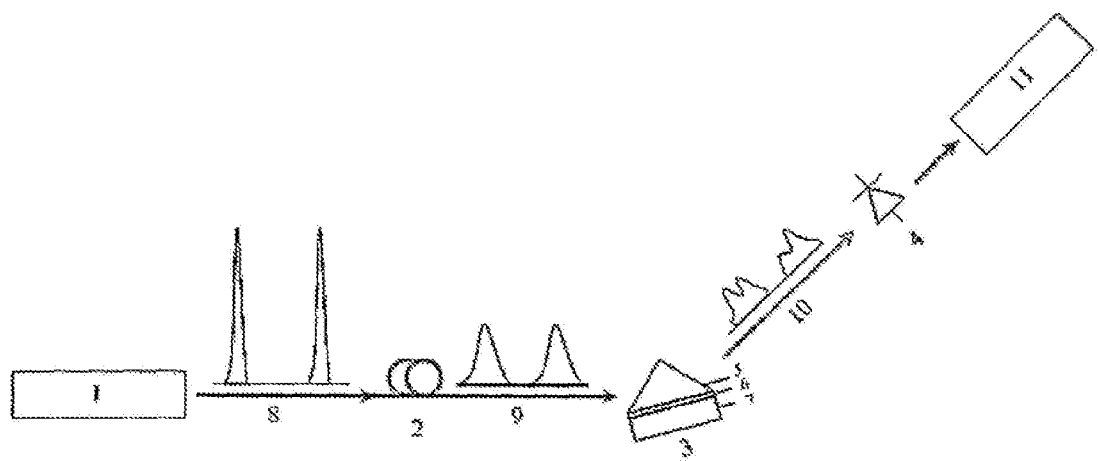
FIG. 1 is a schematic diagram illustrating a high-speed real-time SPR measuring system and the operation principle thereof.

In the drawings:
1—coherent broadband pulsed light source
2—dispersive device
3—SPR sensing device
4—detector
5—coupling prism
6—sensor
7—sample pool
8—first pulse
9—second pulse
10—third pulse
11—data processing system

EMBODIMENTS OF THE INVENTION

In the following, the invention will be explained and described in further details in conjunction with the accompanying drawings.

With the development of optical fibers and optical techniques, there has been significant development in novel light source techniques and optical signal processing techniques.

At present, the conventionally coherent broadband light sources include mode-locked pulse laser and supercontinuum source. The mode-locking technique includes active mode-locking and passive mode-locking. In active mode-locking, an intensity or phase modulator is commonly used to repeatedly modulate the amplitude or frequency (phase) of the oscillating optical field in a cavity, thereby continuously generating additional sidebands. As a result, the output optical signal has a broader coherent spectrum and is made up of a train of pulses in the time-domain composing narrow pulseshape. Passive mode-locking is an all-optical non-linear technique, in which the short pulses are not generated by using active devices in the cavity, such as modulators. In passive mode-locking, pulses are compressed according to the dependence of the intensity of the pulses and the performance of the non-linear optical devices, and narrow optical pulses can be obtained. As a rather well-developed technique, mode-locking can be easily implemented with various mechanisms, such as solid-state mode-locking laser, optical fiber mode-locking laser, semiconductor mode-locking laser and so on. With the currently available mode-locking techniques, a pulse source with width less than tens of fs, peak power more than 1 kW, repeating frequency more than 10 GHz, time jitter less than a few fs and high duty cycle can be achieved. The central wavelength of the generated pulse may be in visible band or infrared band, according to the gain medium of the laser. Well-developed products using different mode-locking techniques in various bands are available now.

Supercontinuum is generated when a high-power short optical pulse propagates through a non-linear medium, which is a phenomenon that the spectrum of the pulse is broadened by the joint effect of the group velocity dispersion of the material and the non-linear effects including self-phase modulation, cross-phase modulation, stimulated Raman scattering and four-wave mixing. And supercontinuum sources are optical sources with a spectrum of up to hundreds or thousands of nm realized based on that, and the spectrum of which can be even wider than that of the mode-locked pulse laser and may cover the wavelength range of visible or infrared band, commonly used by SPR systems. The input short optical pulse is usually generated by mode-locked lasers or Q-switching lasers and then amplified by an optical amplifier. And the non-linear media are generally non-linear photonic crystal fiber, dispersion tapered fiber, dispersion flattened fiber or dispersion shifted fiber optic. Supercontinuum has been applied to optical communications such as all-optical sampling, all-optical conversion, optical wavelength division multiplexing (OWDM) and optical time division multiplexing (OTDM), due to the fact that it can provide ultrashort optical pulses in a very wide wavelength range. At the same time, commercial products are launched by Koheras and Fianium.

There are two methods that usually used to generate Supercontinuum in optical fibers. In the first method, optical fibers with anomalous dispersion are utilized, and the spectrum is broadened by compressing the pulses using the soliton-effect. While in the second method, optical fibers with normal dispersion are used, and the spectrum is broadened by using frequency chirp caused by the optical Kerr effect. The second method may be readily used to generate linear-chirped short optical pulses.

In the embodiments of the invention, the term "time-domain monotonous chirp" used hereafter refers to monotonous expansion of pulse frequencies in the time domain. Said monotonous expansion is the case where one frequency component of the pulse broadened in the time domain, corresponds to only one time position. In a linear chirp, time position of each frequency component in the chirped pulse is linearly related to the relative frequency deviation.

As for optical signal processing techniques, what the embodiment principally employed are the dispersion effect and the chirping technique of optical pulses.

When a beam of light waves interacts with bound electrons of a dielectric medium, the response of the medium usually depends on the frequency of the light wave, which is referred to as dispersion. In the case of a pulse propagating through a dispersive medium or component, different frequency components experience different propagation time delays. Numerous materials and devices can be used to realize the dispersion effect, such as optical fiber, chirped fiber grating, grating pair, prism pair, ultrashort pulseshaper and so on.

Taking the optical fiber as an example, when the optical field of an unchirped Gaussian pulse (normalized amplitude of the optical field U is shown in Equation (3)) is incident on an optical fiber, the amplitude of the optical field after propagating a distance z in the fiber is given in equation (4).

$$U(0, t) = \exp\left(-\frac{t^2}{2T_0^2}\right) \tag{3}$$

$$U(z, t) = \frac{T_0}{(T_0^2 - i\beta_2 z)^{1/2}} \exp\left(-\frac{t^2}{2(T_0^2 - i\beta_2 z)}\right) \tag{4}$$

In the above equation, $T_o$ is a half-width parameter of the input pulse (taken at 1/e of the intensity peak), $\beta_2$ is the group-velocity dispersion parameter, z is the propagation distance along the fiber. It can be seen that the Gaussian pulse still maintains the Gaussian profile during propagation, though the half-width parameter $T_1$ of the pulse increases with z, which is shown in equation (5).

$$T_1(z) = T_0[1+(z/L_D)^2]^{1/2} \tag{5}$$

where, $L_D = T_0^2/|\beta_2|$ is the dispersion length. And equation (4) may be rewritten as:

$$U(z, t) = |U(z, t)|\exp[i\phi(z, t)] \tag{6}$$

$$\text{where, } \phi(z, t) = -\frac{\text{sgn}(\beta_2)(z/L_D)}{1+(z/L_D)^2}\frac{t^2}{T_0^2} + \frac{1}{2}\arctan\left(\frac{z}{L_D}\right) \tag{7}$$

$$\delta\omega(t) = -\frac{\partial\phi}{\partial t} = \frac{2\text{sgn}(\beta_2)(z/L_D)}{1+(z/L_D)^2}\frac{t}{T_0^2} \tag{8}$$

It can be seen from equation (8) that the instantaneous frequency of the optical field after propagating in the fiber $\delta\omega$, i.e., the frequency deviation from the central frequency, is proportional to the time t. Thus, the frequencies of all the time positions in the pulse are no longer the same and are proportional to the time position, which is referred to as linear frequency chirp.

With the development of optical pulse techniques since the late 80 s, techniques for controlling pulse shape are well-established. With the above optical dispersion and pulse phase control techniques, it is possible to obtain broadened optical pulse with linear chirp by letting the short pulses generated by a coherent pulse source pass through a dispersive device.

The light sources used in all the SPR wavelength interrogation systems are incoherent broadband light sources so far and the SPR response is retrieved by measuring the reflected spectrum using instruments such as monochromator or optical spectrum analyzer, and the interrogation speed is rather slow. If a coherent broadband light source is used instead, the pulse can be broadened into a chirped pulse through a dispersive component in which case the frequency components are mapped with the time positions within one pulse, and the SPR response in the frequency domain can be obtained by measuring the distribution of the pulse shape in the time domain. And the pulseshape can be detected real-time in a simple way using high-speed photoelectric detector.

An embodiment of a high-speed real-time SPR measuring system is illustrated in FIG. 1. The system includes a coherent broadband pulse source 1 with linear-polarized light as output, a dispersive device 2, an SPR sensing device 3, a detector 4 and a data processing system 11, all of which are sequentially arranged in the light path. A first pulse 8 generated by the coherent broadband pulse source 1 is turned into a second chirped pulse 9, after propagating through the dispersive device 2. The second pulse 9 is incident on the SPR sensing device 3 at a fixed angle, and a third pulse 10 is obtained after being reflected from the SPR sensing device 3. The detector 4 receives the third pulse 10 and transmits the obtained data to the data processing system 11 for processing.

The coherent broadband pulse source 1 is a femtosecond pulse laser, which generates pulses with a repetition rate of 50 MHz and wavelengths centered at 1550 nm. The pulse is Gaussian shaped with a width of 200 fs and has a spectrum of 26 nm (both taken at 1/e of the intensity peak).

Figure 2:
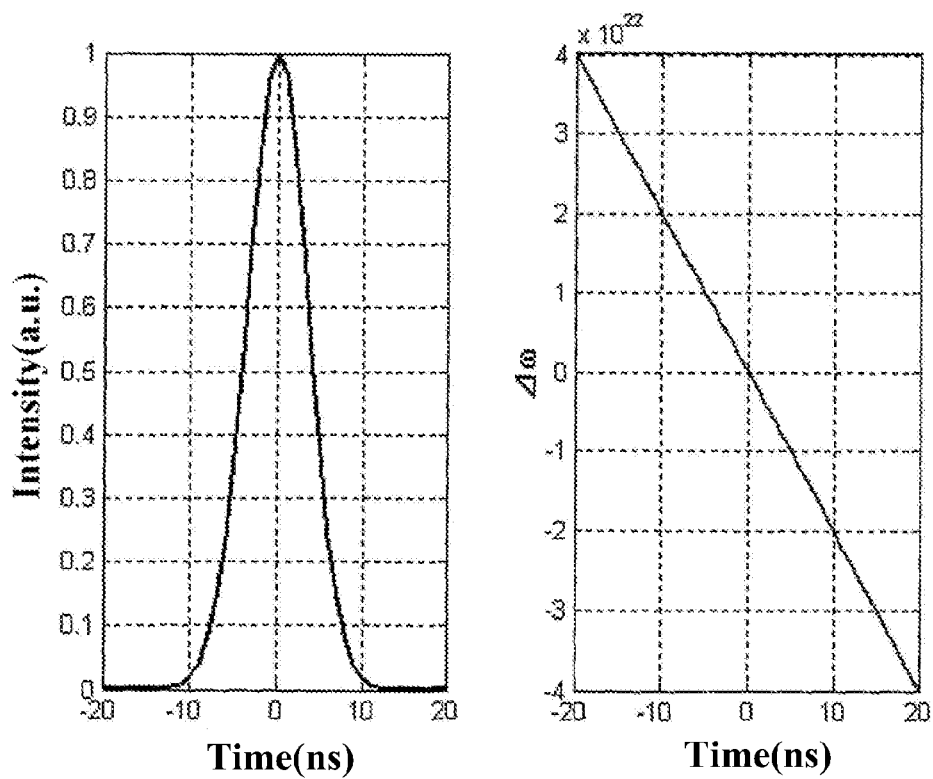
FIG. 2 illustrates the time-domain pulseshape and instantaneous frequency distribution of the chirped input pulse.

A spool of standard single-mode optical fiber is used as the dispersive device, the length of which is 25 km, and the group-velocity dispersion parameter $\beta_2$ of which is $-20$ ps$^2$/km. The pulse is broadened to 10 ns and the pulse shape and distribution of chirp are shown in FIG. 2. It can be seen from FIG. 2 that the amount of change in the instantaneous angular frequency is proportional to the time, $\Delta\omega=2\times10^{22}\,\Delta t$ rad/s$^2$. It will be appreciated by those skilled in the art that the dispersive device may also be a dispersion compensation fiber (DCF), a chirped fiber grating, a grating pair, a prism pair or an ultrashort pulseshaper etc.

Conventional Kretschmann configuration is used for the SPR sensing device. The coupling prism 5 is made of ZF-4 glass, with a refractive index of 1.69855 (at the wavelength of 1550 nm), and the sensing layer 6 is a layer of gold film with a thickness of 50 nm.

The solution under detection in the sample pool 7 is a 1% Ethanol-water solution with a refractive index of 1.3303. The running buffer is water with a refractive index of 1.33.

The detector 4 is a high-speed photodetector, and the PIN photodiode detector utilized in the embodiment has a bandwidth of 40 GHz and a response time of 9 ps, which corresponds to a wavelength of 0.2 nm. It will be appreciated by those skilled in the art that other high-speed photodetectors such as avalanche photo diode (APD) may also be used.

In the measuring system, the coherent broadband pulse source may also be other Supercontinuum sources and mode-locked lasers. Generally, the coherent broadband pulse source has the following functions: (i) the output spectrum thereof comprises frequency components that may excite SPR effect on the SPR device; (ii) the output spectrum covers a certain range and comprises lots of frequency components; (iii) the output spectrum is coherent, which indicates a pulse shape in the time domain; (iv) the output light is a train of pulses with high repeating frequency, which reaches to the order of MHz or even GHz, and a single pulse may be used for one measurement so the corresponding interrogation speed reaches to the order of MHz or even GHz; (v) the output pulse sequences are of high stability, that is, the repeating frequency of the pulses is stable; the starting time of each pulse in the sequences is strictly periodic, stable and accurate; both the time-domain pulseshape and frequency domain spectrum for each pulse in the sequences are the same; (vi) the width of the output spectrum determines the detection range; (vii) the output light is linear polarized TM light. If the output of the coherent broadband pulse source is not linear polarized as required, a polarizing device has to be employed before it is incident on the SPR device.

The dispersive device may also be a chirped optical fiber grating, a grating pair, a prism pair or an ultrashort pulseshape controller. The dispersive device is used to perform the following functions: (i) the dispersive device makes the measuring pulse to be time-domain chirped before it arrives at the detector; time domain positions in the pulse shape may correspond to the frequency domain wavelengths; if time-domain linear chirp is used, the time domain positions in the pulse shape are linearly mapped to the frequency domain wavelengths; (ii) the dispersive device causes time-domain broadening of the measuring pulse before it arrives at the detector, which will improve the time resolution (i.e., wavelength resolution) of the signal waveform; on the other hand, the broadened pulse should not overlap with each other in time domain in the sequences.

The dispersive device may be arranged before the SPR device, such that the incident pulse is broadened and chirped before exciting the SPR effect. And the dispersive device may also be arranged after the SPR device to broaden and chirp the pulse modulated by the SPR effect. It is also possible to use one or more dispersive devices before and after the SPR device respectively to collectively broaden and chirp the measuring pulse. Alternatively, the dispersive device may be omitted, if the output of the selected coherent broadband pulse source is linearly chirped and broadened, and meets the resolution requirement of the detecting system.

The SPR sensing device comprises various configurations which may excite the SPR effect. All kinds of SPR configurations are applicable in the measuring method of the embodiment, such as the conventional single-layer SPR structure, Long Range Surface Plasmon Resonance (LRSPR), Coupled Plasmon Waveguide Resonance (CPWR), Waveguide Coupled Surface Plasmon Resonance (WCSPR). The SPR device further comprises an optical device for coupling the incident beam and reflected beam into and out of the SPR device. When the incident light is not polarized, a polarization control device is further arranged before the SPR device for letting the measuring light to be TM polarized.

The detector is generally used to perform the following functions: (i) the detector converts the optical signal into electrical signal so as to perform signal storage and processing; (ii) the detector preferably has high response speed, thus, it is possible to measure the fast changes in the input pulse shape, thereby to distinguish changes in the response over fine frequency intervals.

The data acquisition and processing unit is generally used to perform the following functions: (i) acquiring time-domain amplitude information of each electrical pulse signal detected, according to the repeating frequency of the coherent broadband pulse source; (ii) the acquisition of each pulse has to be strictly synchronous to the repeating frequency of the pulses, that is, the time positions of the acquired pulses have to be the same; (iii) establishing a one-to-one correspondence relationship between the time position of each pulse and the optical frequencies of the light, according to the chirp property of the pulse obtained using the light source and the dispersive device; and (iv) comparing the detected pulseshape with the pulseshape having no SPR effect, in which case the amplitude data in the time domain is converted into the corresponding SPR spectrum responses, thereby obtaining information of the SPR effect.

A measuring method for the above high-speed real-time SPR measuring system is as follows:

First, the SPR device is removed from the light path, and the output of the femtosecond pulse laser is coupled into the single-mode fiber. The width of the pulse after propagating in the single-mode fiber is broadened from 200 fs to 10 ns and the pulse is linearly chirped. The chirped coherent broadband pulse without passing through the SPR device is received by the PIN detector as a second time-domain signal $i_{no\_SPR}(t)$.

Next, the SPR device injected with the sample under detection is placed in the light path. The laser emitted by the single-mode fiber is incident on the coupling prism 5 at a fixed angle. The reflected beam is received by the PIN detector and the optical signal is converted into an electrical signal, which is a first time-domain signal $i_{SPR}(t)$.

Another method of obtaining the first and second time-domain signals using the above detection system is as follows:

First, the incident angle of the pulse emitted by the single-mode fiber is adjusted based on the different sample under detection. The pulse is then incident at the fixed angle on the coupling prism 5 and the SPR device, and another sample with distinctly different properties from the sample under detection is filled, e.g., air, in which case, the SPR effect doesn't occur as the SPR condition is not met. At this point, the laser pulse has a width broadened from 200 fs to 10 ns and is linearly chirped without modulated by SPR effect. The reflected beam is received by the PIN detector and the optical signal is converted into an electrical signal, and a second time-domain signal $i_{no\_SPR}(t)$ is thus obtained.

Next, the sample under detection is filled into the SPR device. The pulse emitted from the single-mode fiber is incident on the coupling prism 5 at the fixed angle. The reflected beam is received by the PIN detector where the optical signal is converted into an electrical signal, and a first time-domain signal $i_{SPR}(t)$ is obtained.

Based on the aforementioned parameters of the laser and the fiber, $\Delta\omega = 2\times10^{22}\,\Delta t$ rad/s² holds for each pulse. Since $\Delta\lambda/\lambda_0 = \Delta\omega/\omega_0$, it is appreciated by those skilled in the art that the time domain pulseshape may be transformed into the frequency domain, and the reflectivity in the frequency domain is $$R(\lambda) = \frac{i_{SPR}(\lambda)}{i_{no\_SPR}(\lambda)},$$

which will be the basis of analysis.

Figure 5:
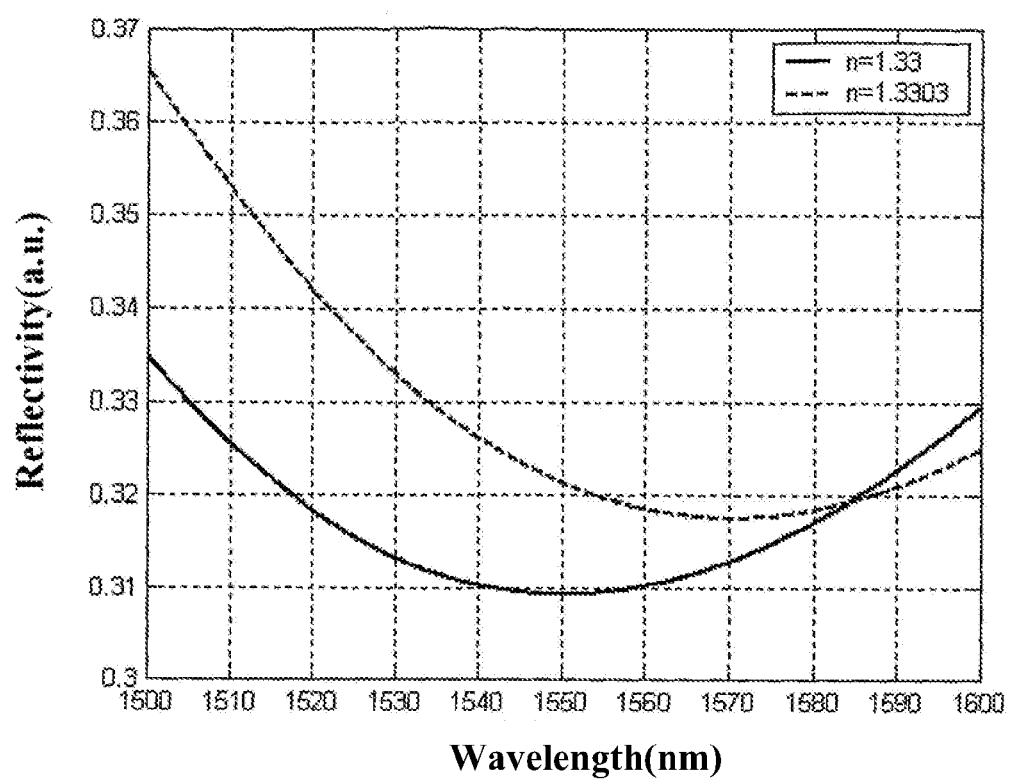
FIG. 5 is the SPR frequency responses according to FIGS. 2 and 4, at different indices of refraction of the detected layer.
Figure 6:
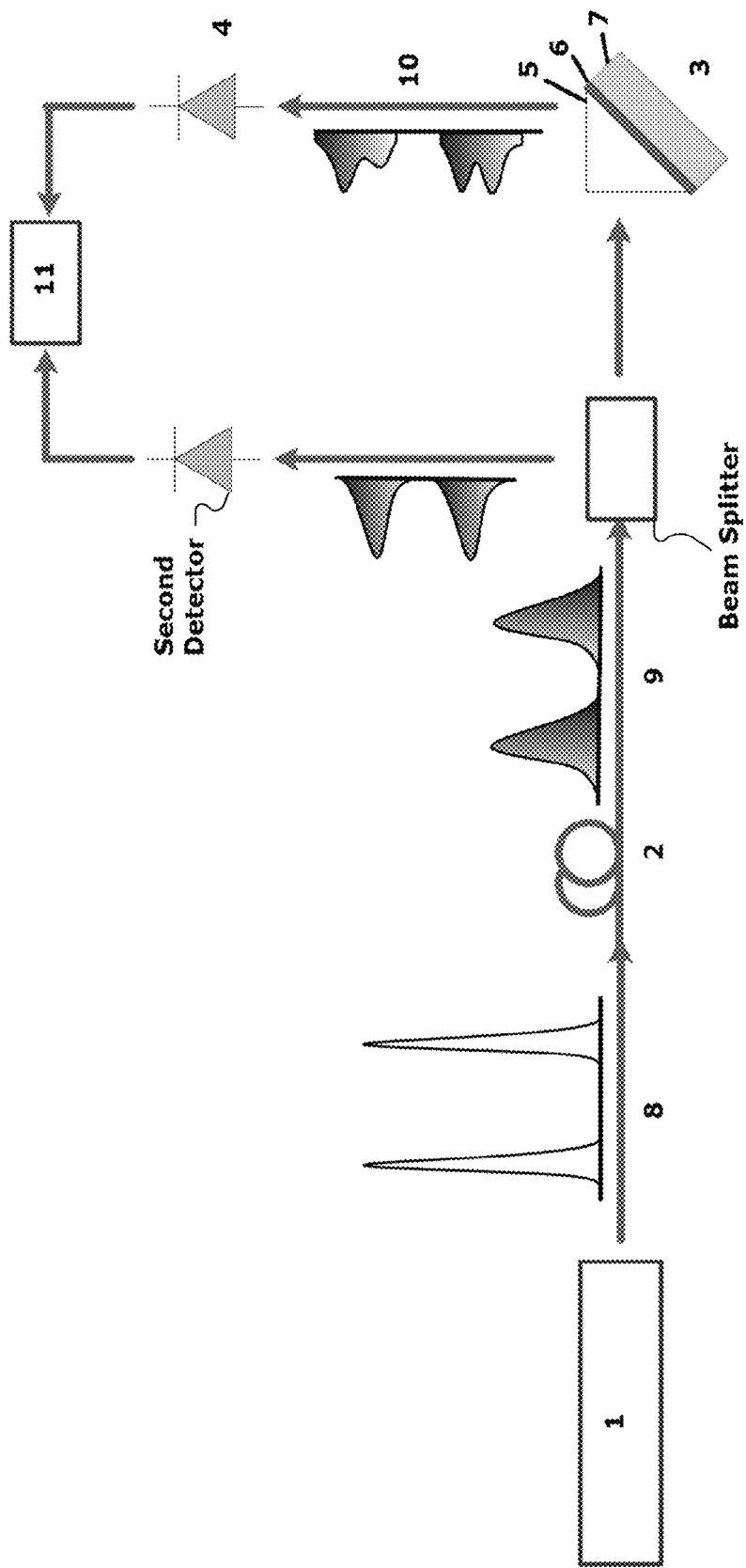
FIG. 6 is another schematic diagram illustrating a high-speed real-time SPR measuring system.

Alternatively, the reflectivity in the time domain is $$R(t) = \frac{i_{SPR}(t)}{i_{no\_SPR}(t)},$$

where $i_{SPR}(t)$ is the chirped pulseshape reflected by the SPR device, which is the first time-domain signal; $i_{no\_SPR}(t)$ is the chirped pulseshape that not modulated by the SPR effect, which is the second time-domain signal and also referred to as the background signal. The effect due to the background can be eliminated by dividing the first time-domain signal by the second time-domain signal. After that, a notch may be found at the position where SPR occurs in the time-domain reflectivity function. After being converted to the frequency domain according to the mapping factor, the same notch may be found at the corresponding wavelength, which is shown in FIG. 5. The conversion from the time domain to the frequency domain is discussed above, and the analysis can then be performed. Analysis on the frequency domain SPR signals is well-known to those skilled in the art and will not be elaborated here.

Figure 3:
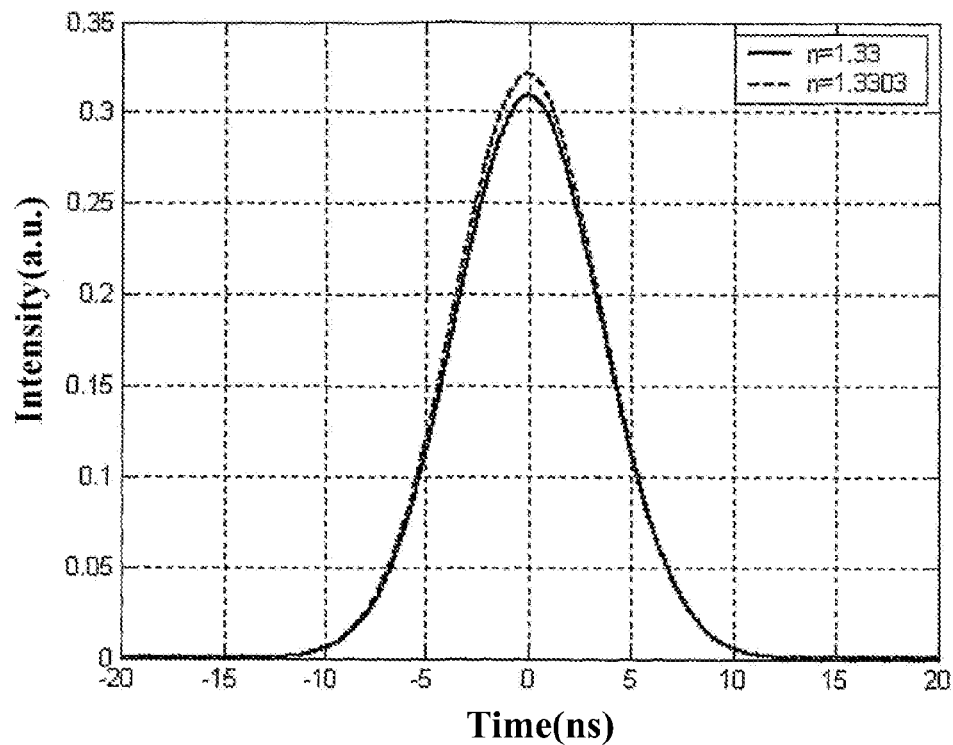
FIG. 3 illustrates time-domain shapes of the chirped pulses modulated with the SPR effect for different indices of refraction of the detected layer.
Figure 4:
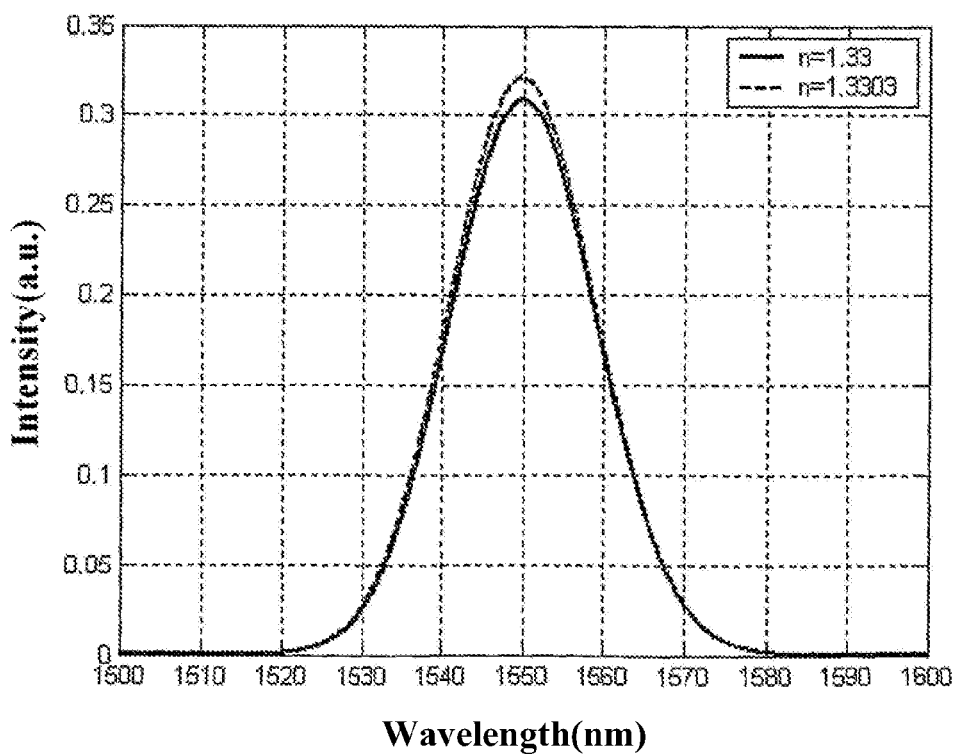
FIG. 4 illustrates distribution of the frequency of the SPR-modulated pulse for different indices of refraction of the detected layer of FIG. 3.

In the embodiment, the incident angle is fixed at 52.411°, which is the SPR excitation angle for the wavelength of 1550 nm. A suitable incident angle can be chosen by those skilled in the art according to different incident wavelengths. FIG. 3 illustrates the pulseshapes with the modulation of the SPR effect, which are the SPR responses, to the Ethanol-water solution and the running buffer water respectively, of the sensing layer 6, which is a gold film. The corresponding intensity spectrums of the pulse with the SPR effect are shown in FIG. 4. The SPR spectral response is obtained by the comparison with the background signal and is illustrated in FIG. 5. Therefore, those skilled in the art may obtain information of the sample, such as the refractive index, using the data processing method in the wavelength interrogation scheme.

Furthermore, another measuring system with a different structure may be designed based on the embodiment of the measuring system described above. A second PIN detector is used in this system. The single-mode fiber has to be arranged in the light path between the femtosecond pulse laser and the SPR device. A beam-splitter is added between the single-mode fiber and the SPR device, where coherent broadband pulse emitted by the single-mode fiber is split into two beams. One of the split chirped pulse beams is incident on the SPR device under detection, and the other beam is directly incident onto the second PIN detector. The detection result of the second PIN detector is analyzed and processed by the data processing system.

Alternatively, the second PIN detector may also be a photodetector such as an Avalanche Photodiode (APD) detector. The beam-splitter may be an optical beam-splitter, a directional fiber coupler and so on.

Accordingly, the measuring method for the second detection system is as follows:

First, the output of the femtosecond pulse laser is coupled into the single-mode fiber. With the dispersion of the single-mode fiber, the pulses are broadened from 200 fs to 10 ns and linearly chirped in the time domain.

Next, the chirped pulse beam is split into two beams by the beam-splitter. One of the split beams is incident on the coupling prism 5 at a fixed angle and then received by the PIN detector after being reflected by the SPR device; the optical signal is then translated into an electrical signal, which is the first time-domain signal $i_{SPR}(t)$. The other beam, which doesn't pass through the SPR device, is received by the second PIN detector as the second time-domain signal $i_{no\_SPR}(t)$. The rest of the signal processing is the same as the first scheme.

In the second measuring system, all the dispersive devices for generating the time-domain monotonous chirp are disposed before the SPR device in the light path, which is different from the first detection system. However, there is no need to move the SPR device for each measurement and the first and second time-domain signals may be measured at the same time, which makes faster measurement possible. Meanwhile, the time-dependent system noises may be eliminated, and in the case that the output of the light source is unstable, the effect introduced by the light source may also be removed. Moreover, instead of the absolution value of change, what matters in the measuring system is the relative refractive index of the SPR device and the change, so the intensities of the two beams from the beam-splitter can be different. It will be appreciated by those skilled in the art that the incident light beam may be split into three or more by the beam-splitter based on the specific requirements of the applications, in the case that the detection is not affected.

The embodiments illustrated in the drawings are intended to illustrate, but not to limit, the technical solutions of the measuring method of the SPR sensing and the structure of the measuring system thereof. Though the invention is described in detail with reference to the embodiments, it will be appreciated by those skilled in the art that any modification or equivalent change to the technical solution of the invention does not depart from the spirit and scope of the invention, and is included in the scope of the appended claims of the invention.

The invention claimed is:

1. A Surface Plasmon Resonance (SPR) measuring method, comprising the steps of:
   (1) providing a linear-polarized, coherent broadband pulsed light beam to incident upon a surface of a sample under detection of a SPR sensing device, wherein the coherent broadband pulsed light beam is caused to reflect from the surface of the sample as a reflected light beam;
   (2) applying a time-domain monotonous chirp to the coherent broadband pulsed light beam or the reflected light beam, wherein applying the time-domain monotonous chirp results in a time-domain monotonously chirped light beam; and
   (3) obtaining wavelength information of the SPR, wherein obtaining the wavelength information comprises:
      detecting the time-domain monotonously chirped light beam affected by the SPR effect to obtain a first time-domain signal, and
      detecting the time-domain monotonously chirped light beam unaffected by the SPR effect to obtain a second time-domain signal, wherein
   wavelength information of the SPR is obtained according to the first time-domain signal and the second time-domain signal.

2. The measuring method of claim 1, wherein obtaining the wavelength information of the SPR comprises:
   obtaining a corresponding time position of a change in the time-domain signal according to a comparison between the first time-domain signal and the second time-domain signal; and
   obtaining a corresponding wavelength in the frequency domain of the time position, according to a distribution of frequencies of the time-domain monotonously chirped light beam in the time domain, thus obtaining the wavelength information of the SPR.

3. The measuring method of claim 1, wherein the time domain monotonous chirp is applied to both the incident coherent broadband pulsed light beam and the reflected light beam from the SPR sensing device.

4. The measuring method of claim 1, wherein the method further comprises:
   (4) retrieving SPR information of the sample under detection according to a data processing method used in the wavelength interrogation.

5. The measuring method of claim 1, wherein the time-domain monotonous chirp is a time-domain monotonous linear chirp.

6. The measuring method claim of 1, wherein the coherent broadband pulsed light beam is incident on the surface of the sample at a fixed angle.

7. The measuring method of claim 1, wherein the SPR information of the sample under detection is a change in the refractive index.

8. A SPR measuring system, comprising:
   a coherent broadband pulse source that generates a linearly-polarized, coherent broadband pulsed light beam incident upon a surface of a sample under detection, wherein the coherent broadband pulsed light beam is caused to reflect from the surface of the sample as a reflected light beam;
   a dispersive device that generates a time-domain monotonous chirp, wherein the time-domain monotonous chirp is applied to the coherent broadband pulsed light beam or the reflected light beam, wherein applying the time-domain monotonous chirp results in a time-domain monotonously chirped reflected light beam;
   an SPR sensing device, wherein the surface of the sample is under detection of the SPR sensing device;
   a first detector for receiving the time-domain monotonous chirped light beam, wherein the first detector determines a component of the time-domain monotonously chirped light beam to obtain a first time-domain signal; and
   a data processing system for processing an output of the first detector, wherein the dispersive device is arranged in a light path before the detector, and wherein the data processing system obtains wavelength information according to the output of the first detector.

9. The measuring system of claim 8, further comprising:
   a second detector; and a beam-splitter for splitting the incident light beam into a plurality of light beam; wherein:
      the dispersive device is arranged in a light path between the coherent broadband pulse source and the SPR sensing device,
      the beam-splitter is arranged in a light path between the dispersive device and the SPR device,
      at least a first beam of the plurality of light beams is incident on the sample under detection by the SPR sensing device,
      at least another of the plurality of light beams is directly received by the second detector, and
      the data processing system processes an output of the first and second detectors.

10. The measuring system of claim 9, wherein the beam-splitter is an optical beam-splitter or a directional optical fiber coupler.

11. The measuring system of claim 8, wherein the coherent broadband pulse light source is a supercontinuum source or a mode-locked laser.

12. The measuring system of claim 8, wherein the dispersive device realizes a linear chirp that results in time-domain broadening of the coherent broadband pulse light.

13. The measuring system of claim 8, wherein the dispersive device comprises at least one of spools of optical fiber, chirped fiber gratings, grating pairs, prism pairs, and an ultrashort pulseshaper.

14. The measuring system of claim 8, wherein the first and second detectors are photodetectors.

15. The measuring system of claim 14, wherein the photodetector is a PIN detector or an APD detector.

* * * * *

UNITED STATES PATENT AND TRADEMARK OFFICE
CERTIFICATE OF CORRECTION

PATENT NO.        : 8,416,416 B2
APPLICATION NO.   : 12/745444
DATED             : April 9, 2013
INVENTOR(S)       : Zheng et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 322 days.

Signed and Sealed this
First Day of September, 2015

Michelle K. Lee
*Director of the United States Patent and Trademark Office*